(12) United States Patent
Cho et al.

(10) Patent No.: US 11,326,194 B2
(45) Date of Patent: May 10, 2022

(54) METHOD FOR PRODUCING DIETARY FIBER

(71) Applicant: DAESANG CORPORATION, Seoul (KR)

(72) Inventors: Kyoung Hee Cho, Gyeonggi-do (KR); Ki Chan Kim, Gyeonggi-do (KR); Kyoung Ok Park, Seoul (KR); Hak Jun Kim, Seoul (KR)

(73) Assignee: DAESANG CORPORATION, Seoul (KR)

( * ) Notice: Subject to any disclaimer, the term of this patent is extended or adjusted under 35 U.S.C. 154(b) by 0 days.

(21) Appl. No.: 17/091,763

(22) Filed: Nov. 6, 2020

(65) Prior Publication Data
US 2021/0189446 A1  Jun. 24, 2021

(30) Foreign Application Priority Data
Dec. 20, 2019  (KR) .................. 10-2019-0171600

(51) Int. Cl.
C12P 19/02  (2006.01)
C12P 19/22  (2006.01)
C13K 1/08  (2006.01)
C13K 7/00  (2006.01)

(52) U.S. Cl.
CPC ............... *C12P 19/02* (2013.01); *C12P 19/22* (2013.01); *C13K 1/08* (2013.01); *C13K 7/00* (2013.01)

(58) Field of Classification Search
None
See application file for complete search history.

(56) References Cited

U.S. PATENT DOCUMENTS

2016/0017303 A1* 1/2016 Cascao-Pereira ....... C12P 19/14
                                                                435/99
2017/0335020 A1* 11/2017 Park ...................... C12P 19/04
2021/0189446 A1* 6/2021 Cho ........................ A23L 33/21

FOREIGN PATENT DOCUMENTS

KR      10-0135075 B       1/1998
KR      10-2017-0130721 A  11/2017

* cited by examiner

*Primary Examiner* — Richard C Ekstrom
(74) *Attorney, Agent, or Firm* — Medler Ferro Woodhouse Mills PLLC

(57) ABSTRACT

The present invention provides a method for producing dietary fiber that has a mild sweet taste by reducing sugars and provides by-products having high added values, and dietary fiber produced by the method. The dietary fiber may be produced by including: liquefying roasted dextrin; and adding enzymes including α-amylase, β-amylase, and maltogenic amylase to the liquefied roasted dextrin, and saccharifying the same.

6 Claims, 4 Drawing Sheets

METHOD FOR PRODUCING DIETARY FIBER

RELATED APPLICATIONS

This application claims priority to Korean Patent Application No. 10-2019-0171600, filed on Dec. 20, 2019 in the Korean Intellectual Property Office, the entire disclosure of which is incorporated herein by reference.

BACKGROUND OF THE INVENTION

1. Field of the Invention

The present invention relates to a method for producing dietary fiber, and more specifically, to a method for producing dietary fiber that has a mild sweet taste by reducing sugars and provides by-products having high added values, and dietary fiber produced by the method.

2. Description of the Related Art

As an interest in health is increased, food materials having functionalities are drawing consumer's great attention. Due to such a consumer trend for food, a lot of various foods using food materials having functionalities are recently available in the market.

One of such food materials may include dietary fiber. Dietary fiber refers to an indigestible polymer fiber component which is not decomposed by digestive enzymes in a body, and is mainly distributed in a cell wall of a plant cell or in a shell of a plant seed.

Since the dietary fiber is not absorbed in the body, it has been recognized as having no nutritional value. However, in recent years, as an interest in functional foods has been increased, and physiological functions of dietary fiber, which differ from six major nutrients such as carbohydrates, proteins, fats, vitamins, minerals and moisture, have been recognized, dietary fiber has come to be known as "the seventh nutrient".

Meanwhile, dextrin generally refers to roasted dextrin (pyrodextrin) prepared by heating starch together with a trace amount of acid at 150 to 180° C. to decompose the same. As a conventional technique for producing indigestible maltodextrin using the roasted dextrin, a method for producing indigestible maltodextrin is disclosed in the art (Patent Document 1), which includes introducing activated carbon into liquefied and saccharified dextrin, and reducing a filtration time by removing fine particles.

In addition, a method for producing dextrin containing dietary fiber is disclosed in the art (Patent Document 2, etc.), which includes applying α-amylase to the roasted dextrin, and then applying glucoside transferase and/or β-amylase thereto.

However, the prior arts as described above include a process of adding hydrogen for the purpose of enriching a taste and improving a feel of the tongue. Therefore, the hydrogen addition process has a problem that an additional catalyst should be used and high temperature and high pressure equipment should be used, and thereby causing an increase in production costs due to the additional process.

PRIOR ART DOCUMENT

Patent Document (Patent Document 1) Korean Patent Laid-open Publication No. 10-2017-0130721

(Patent Document 2) Korean Patent Registration Publication No. 10-0135075

SUMMARY OF THE INVENTION

As a result of performing research for solving the above-described problems of the prior art, the present inventors found out that dietary fiber having a mild sweet taste can be produced without a hydrogen addition process by confirming optimal saccharification conditions by using additional enzymes, and the present invention has been completed on the basis of the finding.

Accordingly, an object of the present invention is to provide a method for producing dietary fiber at a high yield by simultaneously using a specific enzyme to change a sugar composition before separation and purification.

Another object of the present invention is to provide dietary fiber produced by the above method.

To achieve the above-described objects, according to an aspect of the present invention, there is provided a method for producing dietary fiber including: liquefying roasted dextrin; and adding enzymes including α-amylase, β-amylase, and maltogenic amylase to the liquefied roasted dextrin, and saccharifying the same.

In addition, according to another aspect of the present invention, there is provided dietary fiber produced by the above method.

According to the method for producing dietary fiber of the present invention, there are advantages that, by adjusting the sugar composition in an injection solution of a raw material, chromatographic separation is easily carried out, such that dietary fiber can be produced at a high yield, as well as sugars are reduced to help suppress an increase in blood sugar after a meal, and manufacturing costs can be reduced through the use of by-products having high added values.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
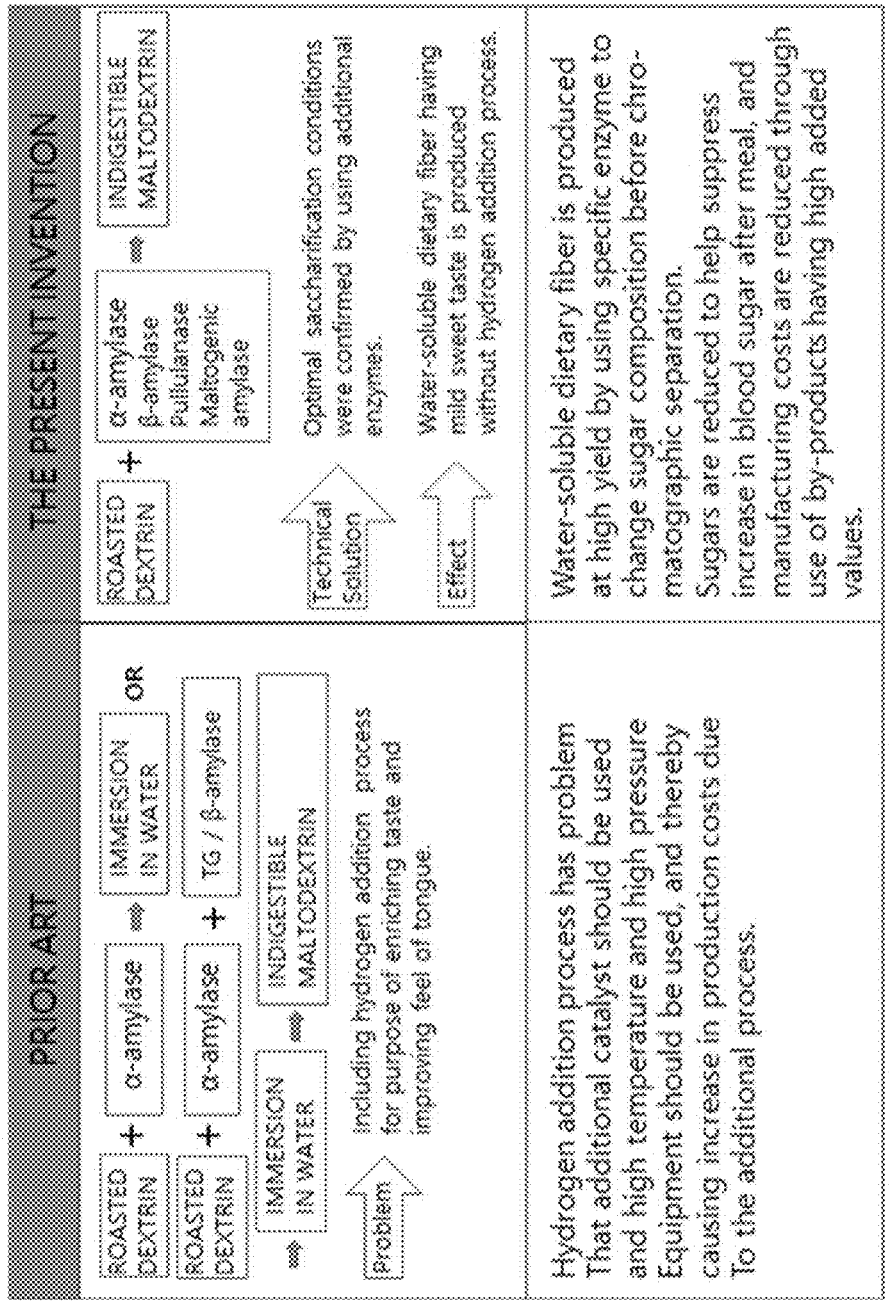
FIG. 1 is a diagram for comparing problems of the prior art with technical characteristics of the present invention.

One embodiment of the present invention relates to a method for producing dietary fiber comprising: (a) liquefying roasted dextrin; and (b) adding enzymes including α-amylase, β-amylase, and maltogenic amylase to the liquefied roasted dextrin, and saccharifying the same.

Dietary fiber is a polymer material of polysaccharides and polysaccharide derivatives, and has properties such as water retentivity, solubility, viscosity, cation exchange properties, and adsorption. That is, dietary fiber has features such as an ability to absorb and retain a certain amount of water, and an increase in volume and swellability due to the retained moisture. The amount of moisture that can be retained by the dietary fiber varies depending on the type and structure of dietary fiber. Cellulose, lignin, and the like have a low water retentivity, whereas pectin, guar gum, and the like have a high water retentivity.

When water-soluble dietary fiber is dissolved in water, it binds to water and becomes a sol with a high-viscosity, thereby playing a role of suppressing a diffusion rate of food ingredients. The viscosity varies depending on a structural change. Dietary fiber has a carboxyl group and a lactic acid group in constituents thereof, such that it has abilities to adsorb cations and to adsorb bile acid, cholesterol, toxic substances and the like.

In terms of physiological functionality, dietary fiber is effective in preventing constipation, hemorrhoids, colon cancer, appendicitis, and the like, and can prevent circulatory system diseases such as high blood pressure, arteriosclerosis, heart disease and the like. In addition, dietary fiber is good for diabetes by suppressing an increase in a blood sugar level, and has an effect of preventing obesity.

The classification method for materials belonging to dietary fiber varies according to scholars. That is, there are methods of classification including: classification based on a chemical structure; classification of dietary fiber consumed in tissues of animals and plants and dietary fiber consumed in each separated form; and classification of water-soluble dietary fiber and water-insoluble dietary fiber based on affinity for water. When classifying into water-soluble and water-insoluble dietary fibers, the water-soluble dietary fiber includes polydextrose, pectin, guar gum, carrageenan, alginic acid, and the like, and the water-insoluble dietary fiber includes cellulose, hemicellulose, lignin, chitin and the like.

In the method for producing dietary fiber of the present invention, as the roasted dextrin used in step (a), any roasted dextrin known in the art may be sufficiently used. For example, it is possible to use roasted dextrin prepared by pre-drying with hot air in a state in which a small amount of acids such as hydrochloric acid, sulfuric acid, or nitric acid is added to corn starch, and then heating to about 130° C. to 180° C., but it is not limited thereto.

In the step (a) of the method for producing dietary fiber according to the present invention, the liquefaction is performed by adjusting the roasted dextrin to pH 5.0 to 6.0, and then maintaining the same at a temperature of 100 to 110° C. preferably 105° C., for 5 to 15 minutes, and preferably 10 minutes.

In the method for producing dietary fiber of the present invention, the saccharification of the step (b) is performed by adding the enzymes under conditions of pH 5.0 to 6.0 and a temperature of 55 to 65° C., preferably 60° C. for 48 to 72 hours, and preferably 50 to 60 hours.

In the step (b) of the method for producing dietary fiber according to the present invention, it is preferable to simultaneously add enzymes including α-amylase, β-amylase and maltogenic amylase. The reason is that, when simultaneously treating the enzymes, the highest dietary fiber total content may be obtained.

In the method for producing dietary fiber of the present invention, the enzyme may further include pullulanase. Even in this case, in order to obtain the highest dietary fiber total content, it is preferable to simultaneously add enzymes including α-amylase, β-amylase, maltogenic amylase and pullulanase.

In the method for producing dietary fiber of the present invention, the α-amylase may be added in an amount of 0.01 to 0.1% (w/w), preferably 0.01 to 0.03% (w/w), the β-amylase may be added in an amount of 0.01 to 0.1% (w/w), preferably 0.01 to 0.03% (w/w), and the maltogenic amylase may be added in an amount of 0.01 to 0.5% (w/w), preferably 0.1 to 0.2% (w/w), based on a total amount of the liquefied roasted dextrin.

In the method for producing dietary fiber of the present invention, the pullulanase may be added in an amount of 0.01 to 0.1% (w/w), preferably 0.01 to 0.03% (w/w), based on the total amount of the liquefied roasted dextrin.

The method for producing dietary fiber of the present invention may further include: (c) filtering the sugar solution obtained in the step (b); (d) decoloring the filtered filtrate by treatment with activated carbon; (e) purifying the decolored filtrate by passing it through an ion exchange resin; and (f) concentrating the filtrate after the purification, followed by performing column chromatography filled with a strongly acidic cation exchange resin to obtain a dietary fiber sugar solution.

The filtration in the step (c) is to remove impurities by performing solid-liquid separation on the sugar solution obtained by saccharification, and the filtration may be sufficiently performed by any method well known in the art such as gravity filtration, pressure filtration, vacuum filtration, and centrifugal filtration, and therefore the filtration method will not be described in detail.

The decolorization in the step (d) may be performed by treating the filtered filtrate with powdered activated carbon, and the activated carbon used in the decolorization is preferably fine powdered activated carbon having a size of 1 to 800 μm, and more preferably 1 to 100 μm, but it is not limited thereto.

In the step (e), in order to remove the impurities such as ionic components in the decolorized filtrate, the purification may be performed by passing the filtrate through a column at room temperature, which is filled with a cation exchange resin, an anion exchange resin, and a resin mixed with the cation and anion exchange resins at a rate of twice a volume of the exchange resin, but it is not limited thereto.

In the step (f), the purified saccharification solution obtained from the step (e) is concentrated, followed by performing column chromatography filled with a strongly acidic cation exchange resin to obtain a water-soluble dietary fiber sugar solution with a high purity.

In the dietary fiber sugar solution obtained through the above processes, a content of water-soluble dietary fiber may be 69% (w/w) or more, and preferably 69 to 75% (w/w).

Another embodiment of the present invention relates to dietary fiber produced by the above method.

The dietary fiber of the present invention has an advantage of helping to suppress an increase in blood sugar levels after a meal due to the reduced sugars.

Hereinafter, the present invention will be described in detail through examples. However, these examples are only intended to specifically illustrate the present invention, and the scope of the present invention is not limited to these examples.

EXAMPLES

Examples and Comparative Examples—Preparation of Water-Soluble Dietary Fiber

Enzymes used in the following examples and comparative examples are α-amylase (Termamyl classic, Fungamyl 800L, Novozymes Co.), amyloglucosidase (Gal-New, Dupont Co.), β-amylase (Secura, Novozymes Co.), pullulanase (Optimax L1000, Dupont Co.), Maltogenic amylase (Maltogenase L, Novozymes Co.).

Further, in the following examples and comparative examples, "%" refers to "% (w/w)" unless specifically mentioned.

Comparative Example 1

35% of roasted dextrin shiny was adjusted to pH 5.0 to 6.0, followed by treating at 105° C. for 10 minutes to perform liquefaction. Herein, as shown in Table 1 below, 0.09% of Termamyl classic (Novo Co.) and 0.34% of Gal-New (Dupont Co.) were simultaneously added and saccharified under conditions at a temperature of 60° C. and pH 5.2 to 5.6 for 50 hours or more (a first step).

The saccharified solution obtained in the above step was filtered, decolorized by powdered activated carbon treatment, and purified by ion exchange resin, followed by concentrating to 50 Bx. Then, the concentrated filtrate was passed through two glass columns (2.5×100 cm) which are filed with a strongly acidic cation exchange resin (Diaion Co., UBK-530, Na+ type) and are connected with each other in series while maintaining at a temperature of 60° C. at a rate of 0.1 S.V., followed by performing fractionation to obtain a water-soluble dietary fiber sugar solution (a second step).

Comparative Example 2

A water-soluble dietary fiber sugar solution was obtained according to the same procedure as described in Comparative Example 1, except that 0.022% of Fungamyl 800L, (Novozymes Co.) and 0.025% of Secura (Novozymes Co.) were used as the enzyme.

Comparative Example 3

A water-soluble dietary fiber sugar solution was obtained according to the same procedure as described in Compara-
tive Example 1, except that 0.14% of Maltogenase L (Novozymes Co.) was used as the enzyme.

Comparative Example 4

A soluble dietary fiber sugar solution was obtained according to the same procedure as described in Comparative Example 1, except that 0.14% of Maltogenase L (Novozymes Co.) and 0.025% of Secura (Novozymes Co.) were used as the enzyme.

Example 1

A water-soluble dietary fiber sugar solution was obtained according to the same procedure as described in Comparative Example 1, except that 0.14% of Maltogenase L (Novozymes Co.), 0.025% of Secura (Novozymes Co.), and 0.022% of Fungamyl 800L (Novozymes Co.) were used as the enzyme.

Example 2

A water-soluble dietary fiber sugar solution was obtained according to the same procedure as described in Comparative Example 1, except that 0.14% of Maltogenase L (Novozymes Co.), 0.025% of Secura (Novozymes Co.), 0.022% of Fungamyl 800L (Novozymes Co.) and 0.02% of Optimax L1000 (Dupont Co.) were used as the enzyme.

Experimental Example

In the following experimental examples, DP1 means glucose, DP2 means maltose, DP3 means maltotriose, and DP4 means maltotetraose.

Experimental Example 1. Analysis of Sugar Composition for Each Saccharification Condition Results of analyzing the sugar composition in the saccharified solution obtained by the first step of adding the enzymes and saccharifying the same in Comparative Examples 1 to 4 and Examples 1 to 2 are shown in Table 1 below.

At this time, the sugar composition analysis was performed wider conditions shown in Table 2 below.

TABLE 1

| Sugar composition | Comparative Example 1 | Comparative Example 2 | Comparative Example 3 | Comparative Example 4 | Example 1 | Example 2 |
|---|---|---|---|---|---|---|
| DP1 | 47.7 | 4.1 | 5.9 | 5.7 | 7.8 | 8.0 |
| DP2 | 5.8 | 27.0 | 26.3 | 27.3 | 30.6 | 31.7 |
| DP3 | 4.6 | 8.4 | 5.7 | 6.6 | 7.6 | 7.2 |
| DP4↑ | 41.1 | 59.0 | 62.0 | 60.4 | 54.0 | 53.1 |

TABLE 2

| Column | Aminex HPX-42A Carbohydrate column (7.8 × 300 mm, BIO-RAD) |
|---|---|
| Column temperature | 80° C. |
| Eluent | Distilled water (D.W) |
| Flow rate | 0.6 mL/min |
| Detector | Refractive Index Detector |

Figure 2:
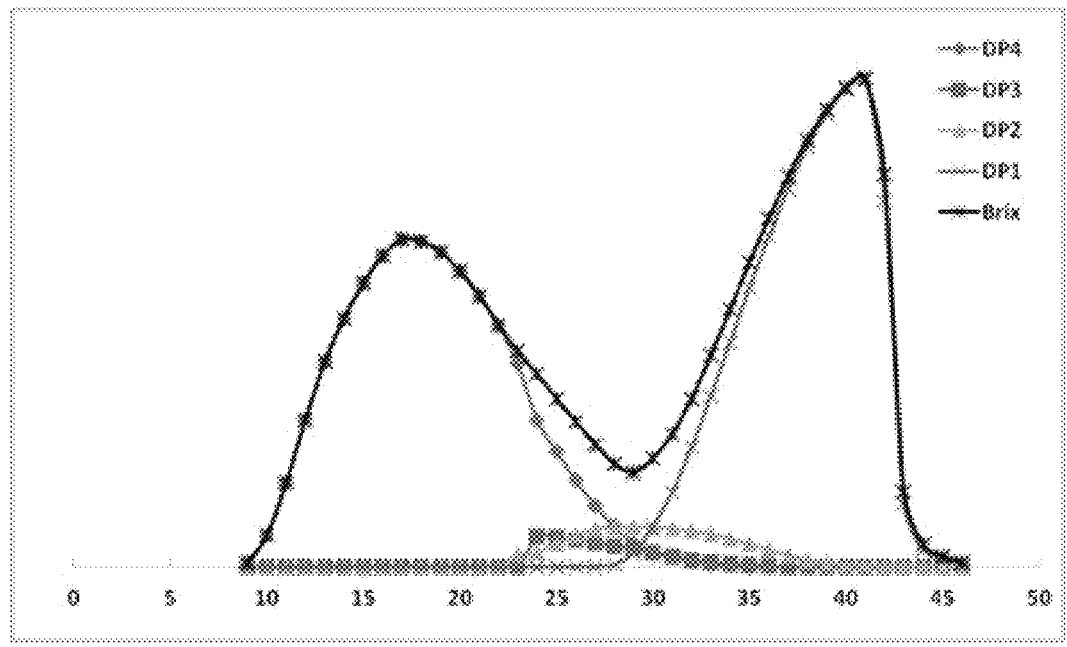
FIG. 2 is a graph illustrating results of analysis of a sugar composition after chromatographic separation of an injection solution (Comparative Example 1) according to Experimental Example 2.
Figure 3:
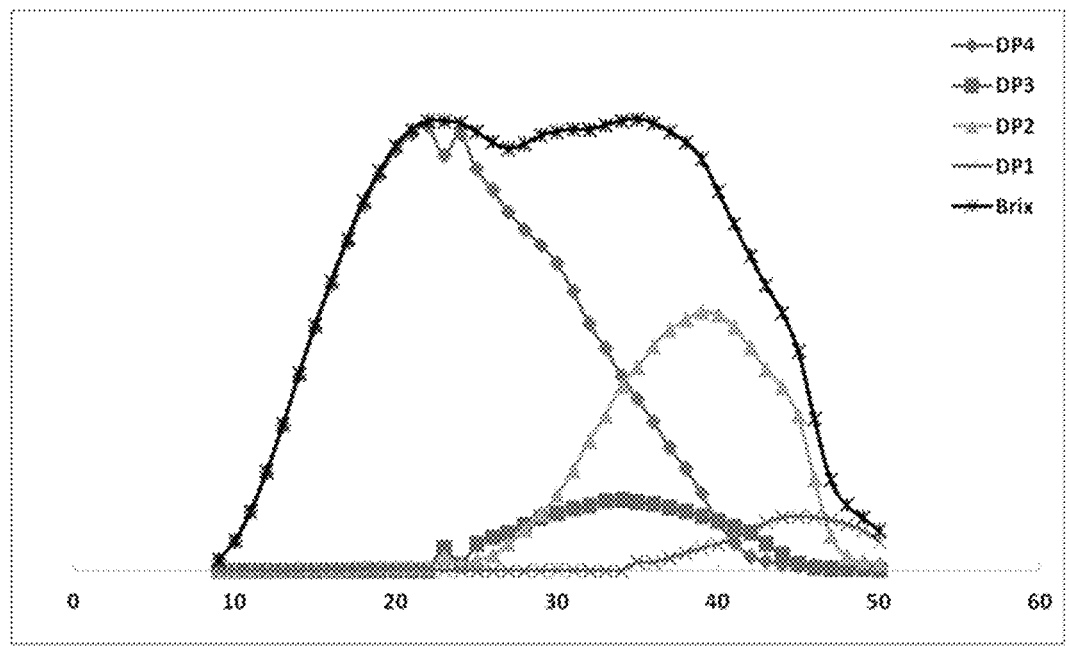
FIG. 3 is a graph illustrating results of analysis of a sugar composition after chromatographic separation of an injection solution (Comparative Example 2) according to Experimental Example 2.
Figure 4:
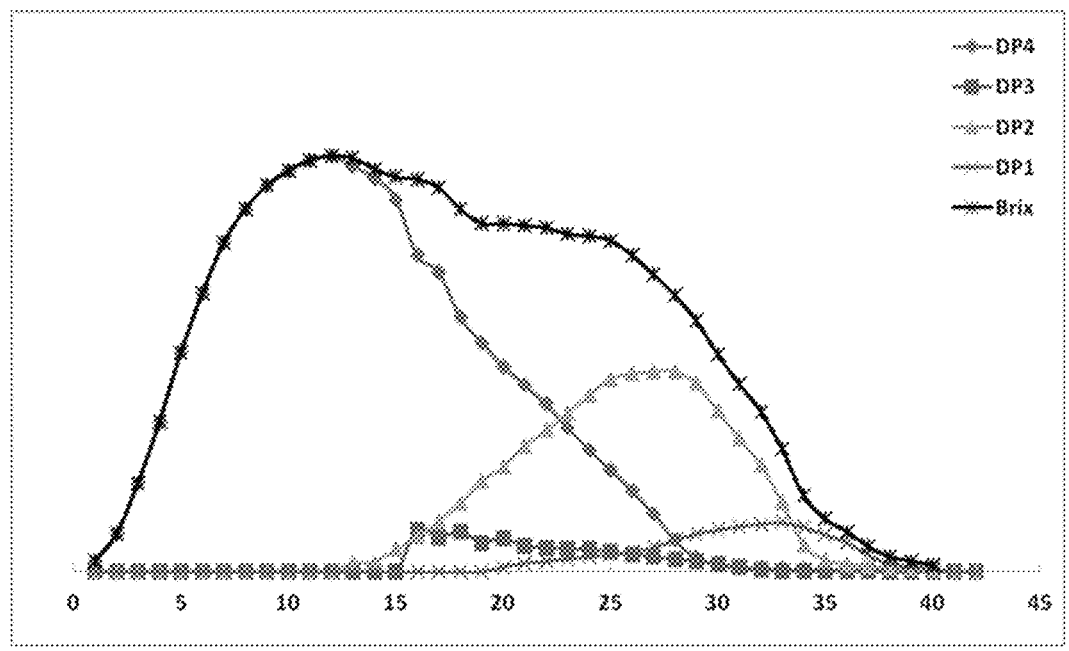
FIG. 4 is a graph illustrating results of analysis of a sugar composition after chromatographic separation of an injection solution (Comparative Example 3) according to Experimental Example 2.
Figure 5:
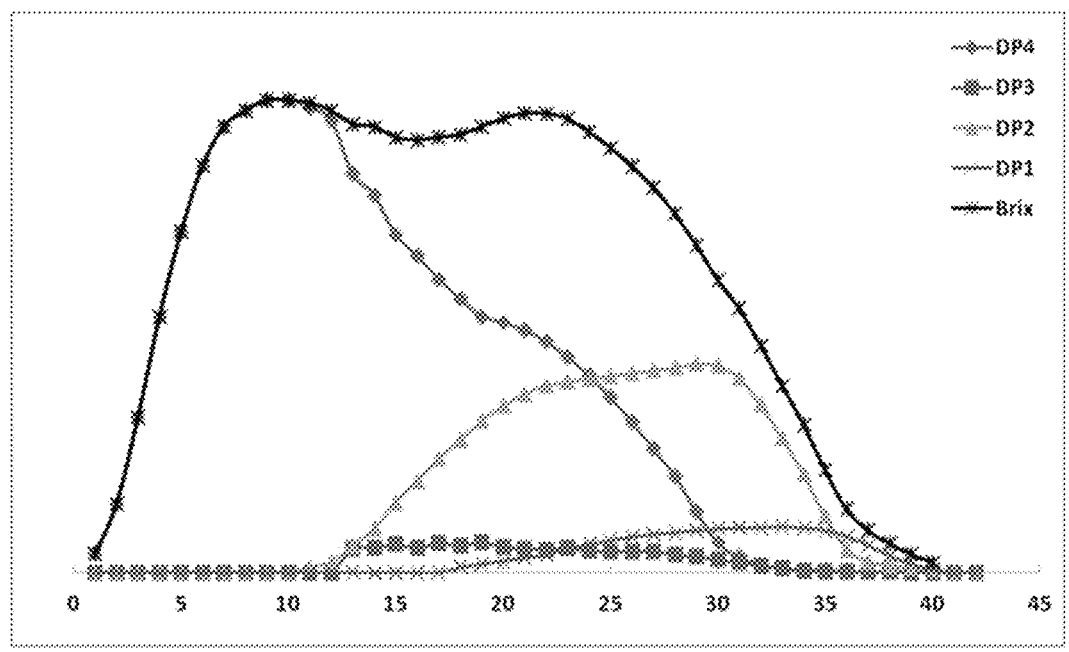
FIG. 5 is a graph illustrating results of analysis of a sugar composition after chromatographic separation of an injection solution (Comparative Example 4) according to Experimental Example 2.
Figure 6:
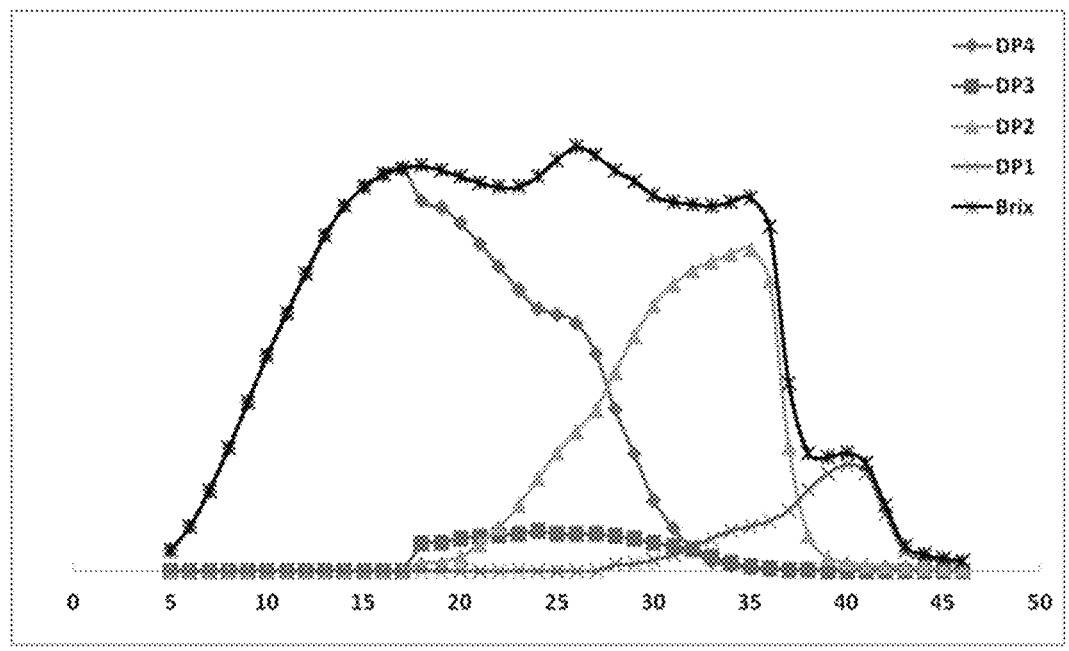
FIG. 6 is a graph illustrating results of analysis of a sugar composition after chromatographic separation of an injection solution (Example 1) according to Experimental Example 2.
Figure 7:
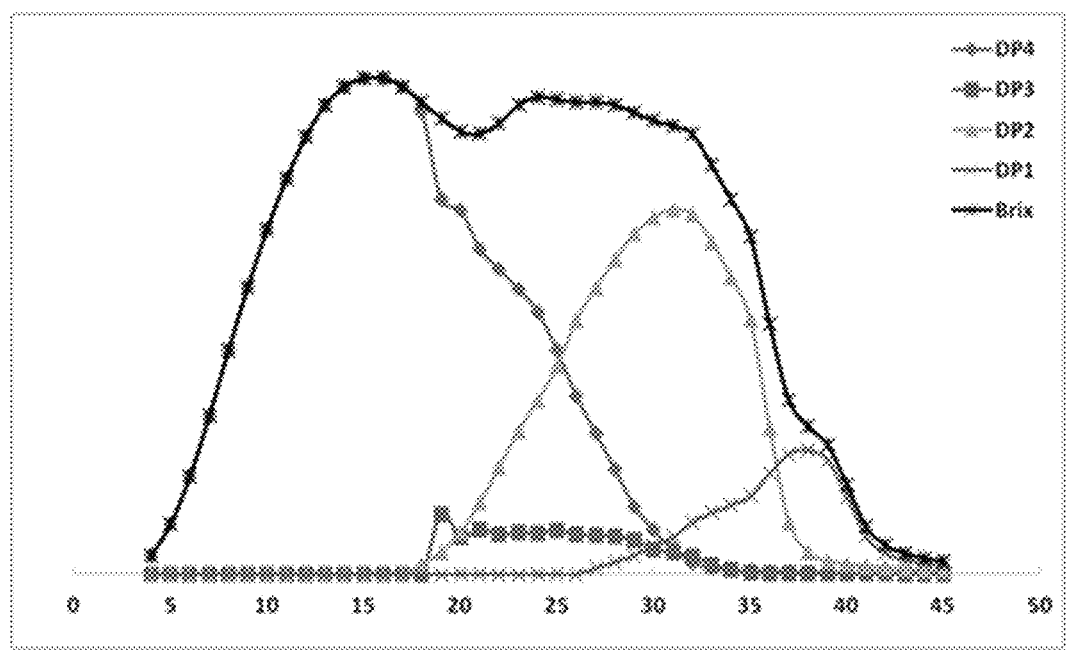
FIG. 7 is a graph illustrating results of analysis of a sugar composition after chromatographic separation of the injection solution (Example 2) according to Experimental Example 2.

Experimental Example 2. Analysis of Sugar Composition after Chromatographic Separation Results of analyzing the sugar composition of the water-soluble dietary fiber sugar solution after performing chromatography and purification (the second step) on the saccharified solution obtained by adding the enzymes and saccharifying the same in Comparative Examples 1 to 4 and Examples 1 to 2 are shown in Table 3 below, and FIGS. 2 to 7.

At this time, the analysis method for DP1 to DP4 was performed by the same procedure as described in Experimental Example 1, and the analysis method for a total dietary fiber (TDF) content was performed by a water-soluble dietary fiber analysis method defined in Korean Food Standards Codex (Method B).

TABLE 3

| Sugar composition | Comparative Example 1 | Comparative Example 2 | Comparative Example 3 | Comparative Example 4 | Example 1 | Example 2 |
|---|---|---|---|---|---|---|
| DP1 | 12.2 | 0.0 | 0.0 | 0.0 | 0.0 | 0.0 |
| DP2 | 8.4 | 7.0 | 7.4 | 11.2 | 9.3 | 10.5 |
| DP3 | 7.9 | 6.2 | 4.1 | 7.0 | 11.1 | 10.1 |
| DP4↑ | 71.5 | 86.8 | 88.5 | 81.8 | 79.6 | 79.4 |
| TDF content | 78.5 | 66.4 | 65.8 | 63.9 | 69.6 | 69.3 |
| Yield (%) | 59 | 59 | 62 | 62 | 60 | 62 |

Analysis Method

TDF content: A water-soluble dietary fiber analysis method defined in Korean Food Standards Codex (Method B)

Experimental Example 3. Analysis of Sugar Composition of By-Product After Chromatographic Separation Results of analyzing the sugar composition of by-products generated after performing chromatography and purification (the second step) on the saccharified solution obtained by adding the enzymes and saccharifying the same in Comparative Examples 1 to 4 and Examples 1 to 2 are shown in Table 4 below.

At this time, the analysis method for DP1 to DP4 was performed by the same procedure as described in Experimental Example 1.

TABLE 4

| Sugar composition | Comparative Example 1 | Comparative Example 2 | Comparative Example 3 | Comparative Example 4 | Example 1 | Example 2 |
|---|---|---|---|---|---|---|
| DP1 | 97.9 | 7.1 | 8.5 | 8.2 | 13.2 | 14.4 |
| DP2 | 0.3 | 42.8 | 41.1 | 43.5 | 55.8 | 58.7 |
| DP3 | 1.9 | 11.9 | 5.3 | 5.3 | 5.4 | 4.8 |
| DP4↑ | 0 | 38.3 | 45.1 | 43.0 | 25.6 | 22.1 |
| Yield (%) | 59 | 40 | 39 | 40 | 49 | 51 |

As shown in the above Table 3, in the conventionally used technique, it can be seen that a separation yield is increased due to a high glucose content in the sugar composition, but the glucose content of a final product is also increased (see Comparative Example 1).

This has problems that it is not suitable for health functional products having health functionalities that help to suppress an increase in the blood sugar after a meal, and if the taste is too sweet, it is difficult to use in foods.

However, as in Examples 1 and 2, when an injection solution having a sugar composition with a high maltose content is subjected to chromatographic separation, the glucose content in the final product may be reduced to less than 1%. Therefore, the sugar content is reduced to one half, and has a mild sweet taste. When maltogenic amylase, α-amylase and β-amylase are simultaneously treated, it can be confirmed that the highest separation yield may be obtained, and it can be seen that it can help to suppress an increase in the blood sugar after a meal.

As shown in the above Table 4, the by-products generated after the chromatographic separation of the saccharified solution prepared in Examples 1 and 2 may be sold as starch syrup, which is a high value-added product, from a generally sold low-cost liquid sugar (Comparative Example 1).

While the present invention has been described with reference to the preferred embodiments as described above, the present invention is not limited to the above-described specific embodiments, and it will be understood by those skilled in the related art that various modifications and variations may be made therein without departing from the scope of the present invention as defined by the appended claims.

What is claimed is:

1. A method for producing dietary fiber comprising:
   (a) liquefying roasted dextrin;
   (b) adding enzymes including α-amylase, β-amylase, and maltogenic amylase to the liquefied roasted dextrin, and saccharifying the same to produce a sugar solution;
   (c) filtering the sugar solution obtained in the step (b);
   (d) decolorizing the filtered filtrate by treatment with activated carbon;

(e) purifying the decolored filtrate by passing it through an ion exchange resin; and
(f) concentrating the filtrate after the purifying, followed by performing column chromatography filled with a strongly acidic cation exchange resin to obtain a dietary fiber sugar solution, wherein the α-amylase is added in an amount of 0.01 to 0.1% (w/w), the β-amylase is added in an amount of 0.01 to 0.1% (w/w), and the maltogenic amylase is added in an amount of 0.01 to 0.5% (w/w), based on a total amount of the liquefied roasted dextrin; and wherein the enzymes are simultaneously added.

2. The method for producing dietary fiber according to claim 1, wherein the enzyme further includes pullulanase.

3. The method for producing dietary fiber according to claim 2, wherein the pullulanase is added in an amount of 0.01 to 0.1% (w/w), based on the total amount of the liquefied roasted dextrin.

4. The method for producing dietary fiber according to claim 1, wherein the liquefaction is performed by adjusting the roasted dextrin to pH 5.0 to 6.0, and then maintaining the same at a temperature of 100 to 110° C. for 5 to 15 minutes.

5. The method for producing dietary fiber according to claim 1, wherein the saccharification is performed by adding the enzymes under conditions of pH 5.0 to 6.0 and a temperature of 55 to 65° C. for 48 to 72 hours.

6. The method for producing dietary fiber according to claim 1, wherein a content of water-soluble dietary fiber in the dietary fiber sugar solution is 69% (w/w) or more.

\* \* \* \* \*